United States Patent [19]

Spencer

[11] Patent Number: 4,533,505
[45] Date of Patent: Aug. 6, 1985

[54] PROCESS FOR THE PREPARATION OF STYRENE DERIVATIVES AND/OR STILBENE DERIVATIVES

[75] Inventor: Alwyn Spencer, Basel, Switzerland

[73] Assignee: Ciba-Geigy Corporation, Ardsley, N.Y.

[21] Appl. No.: 360,017

[22] Filed: Mar. 19, 1982

[30] Foreign Application Priority Data

Mar. 31, 1981 [CH] Switzerland ............... 2179/81

[51] Int. Cl.³ .................. C07C 121/50; C07C 1/20; C07C 1/00
[52] U.S. Cl. ...................... 260/465 R; 260/465 D; 260/465 H; 585/608; 585/642
[58] Field of Search .......... 260/465 R, 465 D, 465 H; 585/608, 642

[56] References Cited

U.S. PATENT DOCUMENTS

| | | | |
|---|---|---|---|
| 3,689,583 | 9/1972 | Kominami et al. | 260/669 R |
| 3,869,500 | 3/1975 | Kominami et al. | 260/465.3 |
| 3,980,713 | 9/1976 | Mitsukuni et al. | 260/612 R |
| 4,108,887 | 8/1978 | Fleck et al. | 260/465 H |
| 4,335,054 | 6/1982 | Blaser et al. | 260/465 G |

Primary Examiner—Delbert R. Phillips
Attorney, Agent, or Firm—Edward McC. Roberts; Kevin T. Mansfield

[57] ABSTRACT

Compounds of the formulae $$Z-CH=CH-Z_1 \text{ (Ia) or}$$
$$CH_2=CH-Z_2-CH=CH_2 \text{ (Ib),}$$

in which Z represents unsubstituted or substituted phenyl or naphthyl, $Z_1$ represents hydrogen or has the same meaning as Z and $Z_2$ represents unsubstituted or substituted phenylene, naphthylene or p-biphenylene or an unsubstituted or substituted stilbene radical, can be obtained in a simple and economical manner in accordance with a novel process by reacting ethylene, under a pressure of 0.1 to 20 bar, in the presence of a base and with the addition of specific palladium catalysts, such as palladium acetate, with appropriate acid halides. The compounds of the formulae Ia and Ib are valuable intermediates, in particular for the preparation of fluorescent brighteners or scintillators.

16 Claims, No Drawings

PROCESS FOR THE PREPARATION OF STYRENE DERIVATIVES AND/OR STILBENE DERIVATIVES

The invention relates to a novel process for the preparation of styrene derivatives and/or stilbene derivatives.

It is known that organic compounds containing vinyl or allyl substituents, inter alia also styrenes and/or stilbenes, can be prepared by a catalytic reaction of appropriate halides with olefins, for example methyl acrylate or ethylene, in the presence of tertiary amines. The catalysts used are preferably mixtures of palladium acetate and triphenylphosphine or tri-o-tolylphosphine. The reaction can also be carried out by first forming a complex from the halide and the catalyst system and then reacting this complex with the olefine in the presence of a tertiary amine. The reaction of halogenobenzenes with ethylene is carried out under pressure, preferably an ethylene pressure of about 1.4 to 14 bar, styrenes and/or stilbenes being formed, depending on the reaction conditions and/or the starting halogenobenzene [cf., for example, U.S. Pat. No. 3,922,299 and J. Org. Chem., 43, 2454 and 43, 2941 (1978)].

According to Bull. Chem. Soc. Japan, 46, 1505 (1973), it is possible to arylate various olefines, inter alia ethylene or propylene, with halogenobenzenes, particularly iodobenzenes, in the presence of palladium black or $PdCl_2$ and an excess of potassium acetate as an acid acceptor. When iodobenzene is reacted with ethylene under pressure, styrene is formed with a selectivity of conversion of 60–90%.

On the other hand, it is known that the reaction of benzoyl chloride with methyl acrylate in the presence of stoichiometric amounts of a nickel(O) catalyst leads to the formation of methyl trans-3-benzoyl acrylate if the reaction mixture is subsequently treated with iodine in methanol. Methyl cinnamate is formed as a by-product in this reaction. Methyl cinnamate is obtained as the main product and methyl benzoyl acrylate as a by-product by reacting a complex formed from benzoyl-palladium chloride and triphenylphosphine with methyl acrylate at 70° to 85° C. in the presence of triethylamine. If only catalytic amounts of the palladium and the triphenylphosphine are employed, the equilibrium of the reaction is shifted in favour of the formation of methyl benzoyl acrylate (the ratio by weight of methyl benzoyl acrylate:methyl cinnamate is approx. 8.3:1) [cf. Transition Met. Chem. 2, 270 (1977) and 4, 298 (1979)]. Finally, it is known from Synthesis, 777 (1977), that the reaction of aromatic acid halides with 1-alkines, catalysed by Pd, leads to alkinyl ketones without decarbonylation.

It has been found that compounds of the formula Ia or Ib

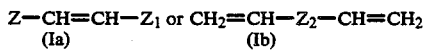
(Ia)            (Ib)

in which Z represents unsubstituted or substituted phenyl or naphthyl, $Z_1$ represents hydrogen or has the same meaning as Z and $Z_2$ represents unsubstituted or substituted phenylene, naphthylene or p-biphenylene or an unsubstituted or substituted stilbene radical, can be prepared by reacting ethylene, under a pressure of 0.1 to 20 bar, in the presence of a base and with the addition, as a catalyst, of palladium metal or palladium compounds which form phosphorus-free labile palladium (O) compounds under the reaction conditions, with a compound of the formula (II) or (III)

(II)            (III)

in which Z and $Z_2$ have the meanings indicated under formula Ia and formula Ib, respectively, and X represents chlorine, bromine or iodine.

The compounds of the formula I can be prepared in a simple and economical manner, under mild reaction conditions and using readily accessible starting materials by means of the process according to the invention. In this process the reaction process surprisingly selectively with decarbonylation of the acid halides of the formula II or III.

The substituents present in groups Z, $Z_1$ or $Z_2$ are substituents which are inert under the reaction conditions. The said groups Z, $Z_1$ or $Z_2$ can be monosubstituted or polysubstituted.

The following are examples of suitable substituents on the groups Z, $Z_1$ and $Z_2$: halogen atoms, formyl, $-CH(OCH_3)_2$, $-CH(OC_2H_5)_2$,

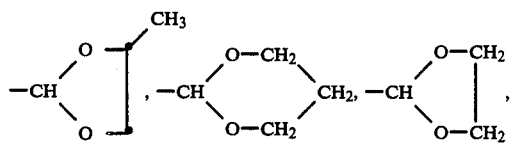

or $-C(X_1)=C(X_2)(X_3)$, in which $X_1$ represents hydrogen, $C_{1-4}$ alkyl, $-CN$ or $-COOR$, $X_2$ represents hydrogen, $C_{1-4}$ alkyl, $-(CH_2)_m-COOR$ or $-(CH_2)_m-CN$ in which $m=1$ to 4, $X_3$ represents phenyl, $-CN$, $-COOR$ or $-CON(R)_2$ and the Rs independently of one another represent $C_{1-12}$ alkyl or phenyl, it being necessary for one of $X_1$ and $X_2$ to be hydrogen; $C_{1-10}$ alkyl groups, $C_{1-16}$ alkoxy groups, phenoxy groups, di-($C_{1-10}$ alkyl)-amino groups, nitro groups or cyano groups; or $-CH_2Cl$ groups, trifluoromethyl groups, benzyl groups, $C_{1-4}$ alkylsulfonyl groups, $-CO-C_{1-10}$ alkyl groups, $-CO$-phenyl groups,

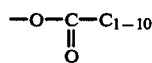

alkyl groups, $-COO-C_{1-10}$ alkyl groups, $-COO$-phenyl groups, phenyl groups or naphthyl groups which can in turn be substituted by halogen atoms, $C_{1-10}$ alkyl groups, $C_{1-10}$ alkoxy groups, di-($C_{1-10}$-alkyl)-amino groups, nitro groups, cyano groups, trifluoromethyl groups, $-CO-C_{1-10}$ alkyl groups, $-CO$-phenyl groups, $-COO-C_{1-10}$ alkyl groups or $-COO$-phenyl groups. Phenyl and naphthyl substituents on the groups Z, $Z_1$ or $Z_2$ are preferably monosubstituted or unsubstituted. Alkyl and alkoxy groups in the substituents mentioned above can be straight-chain or branched, alkyl and alkoxy substituents on the groups Z, $Z_1$ or $Z_2$ having preferably 1 to 8, and especially 1 to 4, C atoms. Examples of halogen substituents are fluorine, chlorine or bromine. The following may be mentioned as examples of substituents of the type defined on the groups Z, $Z_1$ or $Z_2$: the methyl, ethyl, n-propyl, isopropyl, n-, sec.- and tert.-butyl, n-pentyl, 2-pentyl, n-hexyl, n-heptyl, n-octyl and n-decyl groups; the methoxy, ethoxy, n-propoxy. n-butoxy, n-hexyloxy and n-decyloxy groups; the N,N-dimethylamino. N,N-diethylamino. N,N-di-n-propylamino, N,N-di-n-butylamino, N,N-di-n-hexylamino, N,N-di-n-octylamino, N-methyl-N-ethylamino, N-methyl-N-n-propylamino, N-ethyl-N-n-hexylamino and N-ethyl-N-n-butyl-amino groups; the methylsulfonyl and ethylsulfonyl groups; the acetyl, propionyl, butyryl, valeroyl and octanoyl groups; the methyl carboxylate, ethyl carboxylate, n-propyl carboxylate, isopropyl carboxylate, n-butyl carboxylate, n-pentyl carboxylate, n-hexyl carboxylate, n-heptyl carboxylate and n-decyl carboxylate groups; or the groups —CH=CH-phenyl, —CH=C(COOCH$_3$)CH$_2$COOCH$_3$, —CH=C(CH$_3$)COOC$_2$H$_5$, —C(COOCH$_3$)=CHCOOCH$_3$, —CH=C(CN)CH$_2$CH$_2$CN, —CH=CHCOOR and —CH=CHCN, in which R has the meaning indicated above.

In the formulae II and III, X preferably represents bromine and especially chlorine. Alkyl groups R can be straight-chain or branched. Straight-chain alkyl groups R having 1–4, and, in particular, 1 or 2, C atoms are preferred.

Compounds of the formula Ia which can be prepared preferentially are those of the formulae

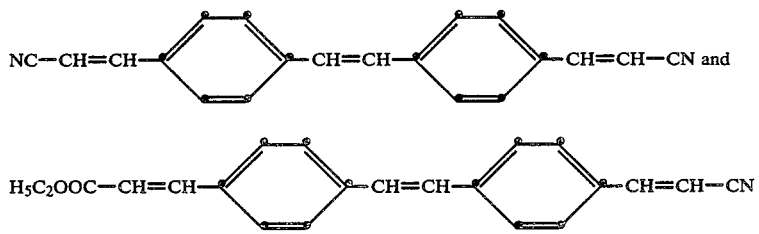

and also the novel compound of the formula

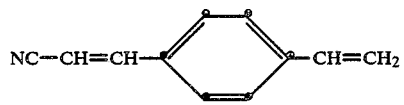

The following are compounds of the formulae II and III which are particularly suitable:

1. Compounds of the formula IIa

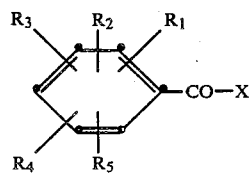

in which X represents chlorine or bromine, R$_1$ represents hydrogen, Cl, Br, F, I, formyl, —CH(OCH$_3$)$_2$, —CH(OC$_2$H$_5$)$_2$,

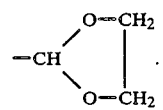

—CH=CHCN, —CH=CH—COO—C$_{1-4}$-alkyl, C$_{1-4}$-alkyl, C$_{1-4}$ alkoxy, phenoxy, di-(C$_{1-2}$-alkyl)-amino, —NO$_2$, —CN, —CF$_3$, C$_{1-4}$ alkylsulfonyl, benzyl, —CO—C$_{1-4}$ alkyl, —CO—phenyl, —OCO—C$_{1-4}$ alkyl, —COO—C$_{1-4}$ alkyl, —COO-phenyl, phenyl, chlorophenyl, bromophenyl, methylphenyl, methoxyphenyl, 1-naphthyl or 2-naphthyl, R$_2$ and R$_3$ independently of one another represent hydrogen, Cl, Br, F, —NO$_2$, C$_{1-4}$ alkyl or C$_{1-4}$ alkoxy, particularly methyl or methoxy, R$_4$ and R$_5$ represent hydrogen or, if R$_1$, R$_2$ and R$_3$ each represent chlorine, bromine, fluorine or methyl, also each represent chlorine, bromine, fluorine or methyl.

Compounds of the formula IIa which are preferred are those in which X represents chlorine, R$_1$ represents hydrogen, Cl, Br, F, I, —CH=CHCN, —CH=CH-COOCH$_3$, —CH=CHCOOC$_2$H$_5$, C$_{1-4}$ alkyl, particularly methyl or ethyl, methoxy, N$^2$,N-dimethylamino, —NO$_2$, —CN, formyl, methylsulfonyl or phenyl, R$_2$ represents hydrogen, Cl, Br, methyl, ethyl, methoxy or nitro, R$_3$ represents hydrogen, Cl, Br, methyl, ethyl or methoxy and R$_4$ and R$_5$ each represent hydrogen, and particularly those in which X represents chlorine, R$_1$ represents —CH=CHCN or —CH=CH—COOC$_2$H$_5$ and R$_2$ to R$_5$ each represent hydrogen.

2. Compounds of the formula IIb (IIb)

in which the group —COCl is in the 1-position or 2-position, R$_6$ and R$_7$ can be attached to the same ring or to different rings, R$_6$ represents hydrogen, Cl, Br, F, methyl, ethyl, methoxy, ethoxy, —CHO, —COCH$_3$, —SO$_2$CH$_3$, —CN, —NO$_2$ or —CH(OCH$_3$)$_2$ and R$_7$ represents hydrogen, Cl, Br, F, methyl, methoxy or —NO$_2$. Preferred compounds of the formula IIb are those in which R$_6$ represents methyl and especially hydrogen and R$_7$ represents hydrogen.

3. Compounds of the formula IIIa (IIIa)

in which R$_8$ represents hydrogen, —CO-phenyl, Cl, Br, F, —CN, —CHO, —NO$_2$ or methyl and R$_9$ represents hydrogen, Cl, Br, F or methyl. Preferred compounds of the formula IIIa are isophthalic and terephthalic acid dichlorides which are unsubstituted or substituted by a methyl or NO₂ group, in particular unsubstituted isophthalic or terephthalic acid dichloride.

4. Compounds of the formula IIIb

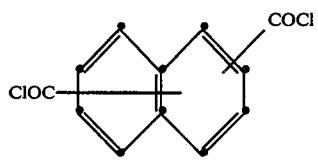

in which the —COCl groups can be attached to the same ring or to different rings. Preferred compounds of the formula IIIb are 1,4-naphthalenedicarboxylic and 2,6-naphthalenedicarboxylic acid dichlorides.

5. The compounds of the formulae IIIc and IIId

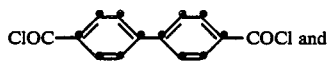

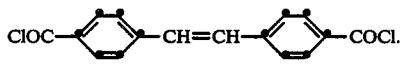

Acid halides which are particularly preferred are the compounds of the formulae IIIc and IIId and also compounds of the formula IIa in which X represents chlorine, $R_1$ represents hydrogen, formyl, methyl, methoxy, Cl, Br or nitro, $R_2$ represents hydrogen, methyl, methoxy, Cl or Br, $R_3$ represents hydrogen or methoxy and $R_4$ and $R_5$ represent hydrogen, or in which X represents chlorine, $R_1$ represents —CH=CHCN, —CH=CHCOOCH₃ or —CH=CHCOOC₂H₅ and $R_2$ to $R_5$ represent hydrogen.

In the process according to the invention, depending on the reaction conditions, mixtures of styrene derivatives ($Z_1$=H) and stilbenes can be formed in the reaction with acid halides of the formula II. The reaction can be controlled mainly by varying the pressure applied. Stilbenes are principally formed under a pressure between 0.1 and 1 bar, preferably 1 bar (normal pressure), whereas under a higher pressure, appropriately a pressure between 5 and 15 bar, preferably 10 bar, in the main styrene derivatives are formed. The reaction with the acid halides of the formula III to give compounds of the formula Ib is preferably carried out under pressure, particularly a pressure between 5 and 15 bar and preferably 10 bar.

The catalysts and also the compounds of the formulae II and III are known or can be prepared by methods which are known per se. With regard to the preparation of compounds of the formulae II and III, cf., for example, "Organikum", 387–388, VEB Deutscher Verlag der Wissenschaften, Berlin 1964.

Examples of palladium compounds of the type defined which can be employed—in addition to palladium metal—are compounds of the formula IV $M^y[PdL_n]^x$  (IV)

in which n represents an integer from 2 to 4, x represents 2⊕ to 2⊖, y represents —(x), M represents a counter-ion if x is not 0 and the Ls represent identical or different phosphorus-free ligands, for example Cl, Br, I, —CN, —NO₃, C₁₋₁₂ alkyl—COO,

NH₃, 2,2'-bipyridyl, o-phenanthroline,

or —NC-phenyl. Examples of suitable compounds of the formula IV are PdCl₂, PdBr₂, Pd(CN)₂, Pd(NO₃)₂, Pd(O₂C—C₁₋₁₂-alkyl)₂, particularly Pd(OOCCH₃)₂,

[Pd(NH₃)₄]Cl₂, [PdCl₄]Na₂.Pd(OOCCH₃)₂(2,2'-bipyridyl), Pd(OOCCH₃)₂-(o-phenanthroline).

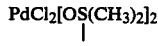

and PdCl₂(NC-phenyl)₂.

Besides the compounds mentioned above, it is also possible to employ palladium compounds in other stages of oxidation, for example bis-(dibenzylideneacetone)-palladium(O) and bis-(isonitrile)-palladium(O) compounds. The following may be mentioned as examples of such isonitriles; bis-(cyclohexyl isonitrile)-palladium(O), bis-(isopropyl isonitrile)-palladium(O), bis-(tert.-butyl isonitrile)-palladium(O), bis-(p-tolyl isonitrile)-palladium(O), bis-(phenyl isonitrile)-palladium(O) and bis-(p-methoxyphenyl isonitrile)-palladium(O). Of these, bis-(dibenzylideneacetone)-palladium(O), bis-(cyclohexyl isonitrile)-palladium(O) and bis-(isopropyl isonitrile)-palladium(O) are preferred.

The catalysts used are preferably PdCl₂, PdBr₂, Pd(OOCCH₃)₂,

Pd(OOCCH₃)₂(2,2'-bipyridyl), PdCl₂(NC-phenyl)₂, bis-(dibenzylideneacetone)-palladium(O) and bis-(cyclohexyl isonitrile)-palladium(O), PdCl₂, palladium acetate and bis-(dibenzylideneacetone)-palladium(O) are very particularly preferred. In general, catalysts are employed in an amount of 0.0001 to 20 mol %, preferably 0.001 to 3 mol %, relative to the compound of the formula II or III.

The bases used in the process according to the invention can be either inorganic or organic compounds which are adequately soluble in the reaction medium. Examples of suitable bases are compounds of the formulae V to VII

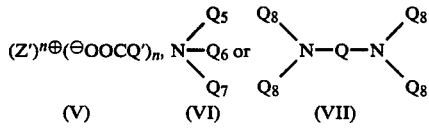

and also cyclic tertiary amines, for example N-methylpiperidine, N-ethylpiperidine, 1,2,2,6,6-pentamethylpiperidine or 4-oxo-1,2,2,6,6-pentamethylpiperidine, 1,4-diazabicyclo[2,2,2]octane (DABCO), N-alkylmorpholines and N-alkylpyrrolidines, such as N-methylmorpholine, N-ethylmorpholine, N-methylpyrrolidine and N-ethylpyrrolidine, or N,N'-dialkylpiperazines, such as N,N'-dimethylpiperazine.

In the above formulae, n represents the number 1 or 2, Q' represents phenyl or $C_{1-17}$ alkyl, Z' represents an alkali metal cation, an alkaline earth metal cation or

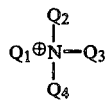

Q represents straight-chain or branched alkylene having 2-6 C atoms, $Q_1$ represents hydrogen, $C_{1-12}$ alkyl, cyclopentyl, cyclohexyl, benzyl or phenyl, $Q_2$, $Q_3$ and $Q_4$ represent identical or different $C_{1-12}$ alkyl radicals, $Q_5$ represents $C_{1-12}$ alkyl, cyclopentyl, cyclohexyl, phenyl or benzyl which can also be substituted, for example by a halogen atom, such as chlorine or bromine or an alkyl or alkoxy group having in each case 1–4, particularly 1 or 2, C atoms, $Q_6$ and $Q_7$ represent identical or different $C_{1-12}$ alkyl and $Q_8$ represents methyl or ethyl.

If Z' represents an alkali metal cation, it is especially the sodium cation and, in particular, the lithium cation. Alkyl groups represented by Q' and $Q_1$ to $Q_7$ can be straight-chain or branched. If $Q_5$ to $Q_7$ represent alkyl groups, these groups advantageously have a total of at least 9 C atoms, while alkyl groups represented by $Q_1$ to $Q_4$ preferably have 1–4 C atoms in each case. The following are examples of compounds of the formulae V to VII: lithium acetate, butyrate and stearate, barium acetate, calcium acetate, potassium stearate, calcium stearate, sodium stearate, lithium benzoate and sodium benzoate, and also the corresponding trimethylammonium, tetramethylammonium, tetraethylammonium and tetra-n-butylammonium salts; triethylamine, tri-n-butylamine, tri-(2-ethylhexylamine), tri-n-octylamine and tri-n-dodecylamine; N-benzyldialkylamines, such as N-benzyldimethylamine, N-benzyldiethylamine, N-(4-chlorobenzyl)-dimethylamine and N-(3-methylbenzyl)-dimethylamine or N-(3-methoxybenzyl)-dimethylamine; N,N,N',N'-tetramethylethylenediamine, N,N,N',N'-tetraethylethylenediamine, N,N,N',N'-tetramethyl-1,3-diaminopropane and N,N,N',N'-tetramethyl-1,6-diaminohexane.

It is preferable to use as bases tertiary amines of the type mentioned above, in particular N-ethylmorpholine or compounds of the formula VI in which $Q_5$ represents 4-chlorobenzyl, 4-methylbenzyl or 4-methoxybenzyl and especially benzyl, and $Q_6$ and $Q_7$ each represent alkyl having 1–4 C atoms, in particular 1 or 2 C atoms, or in which $Q_5$, $Q_6$ and $Q_7$ each represent alkyl having 3–12 C atoms. N-Benzyldimethylamine, N-ethylmorpholine and tri-n-butylamine are particularly preferred.

The reaction temperatures for the reaction according to the invention are appropriately between 0° and 200° C., preferably between 80° and 150° C. If the compounds of the formulae II or III are liquid, the reaction can be carried out without adding a solvent. Preferably, however, the reaction is carried out in an organic solvent which is inert towards the reactants. Depending on the reactants, examples of suitable inert organic solvents are aliphatic, cycloaliphatic or aromatic hydrocarbons which are unsubstituted or substituted by chlorine, such as n-pentane, n-heptane, n-octane, cyclopentane, cyclohexane, benzene, toluene, xylenes and chlorobenzene; aromatic, aliphatic and cyclic ethers, such as anisole, diethyl ether, diisopropyl ether, tetrahydrofuran and dioxane; nitriles, particularly benzonitrile and alkyl nitriles having 2 to 5 C atoms, such as propionitrile and butyronitrile; 3-methoxypropionitrile and 3-ethoxypropionitrile; dialkyl sulfoxides, such as dimethyl sulfoxide and diethyl sulfoxide; N,N-dialkylamides of aliphatic monocarboxylic acids having 1–3 C atoms in the acid part, such as N,N-dimethylformamide and N,N-dimethylacetamide; alcohols having not more than 8 C atoms, such as ethanol, n-propanol and tert.-butanol; aliphatic and cycloaliphatic ketones, such as acetone, diethyl ketone, methyl isopropyl ketone, cyclopentanone and cyclohexanone; esters, such as esters of carbonic acid, for example diethyl carbonate; nitromethane; alkyl or alkoxyalkyl esters of aliphatic monocarboxylic acids having a total of 2–8 C atoms, such as methyl, ethyl, n-butyl and isobutyl acetates, ethyl and n-butyl butyrates and 1-acetoxy-2-ethoxyethane and 1-acetoxy-2-methoxyethane. Preferred solvents are ketones, esters, aromatic and cyclic ethers and aromatic hydrocarbons of the type mentioned above. Polar solvents, in particular, such as ketones and esters, are suitable for the reaction in the presence of inorganic bases. It is very particularly preferred to carry out the reaction in the presence of an aromatic ether or hydrocarbon, in particular anisole, xylenes or toluene.

The compounds which can be prepared in accordance with the invention and their applications are in most cases known. They can, for example, be employed direct as fluorescent brighteners, as intermediates for fluorescent brighteners, or as scintillators. Fluorescent brighteners or scintillators of this type are described, for example, in U.S. Pat. No. 4,108,887 and in British Patent Specification No. 2,015,021. The compounds which have been prepared in accordance with the invention can also be converted into dyes or fluorescent brighteners in a manner which is known per se, if appropriate with the introduction of suitable functional groups, such as amino groups, and/or by sulfonating the aromatic radicals Z, $Z_1$ and $Z_2$ [cf., for example, Encyclopedia of Chemical Technology, 2nd edition, Volume 19, pages 1 to 16]. Stilbenes and stilbene derivatives are also used as additives for adhesives, insecticides or light stabilisers; cf., for example, Chemical Abstracts 78, 39,352; 84, 137,386 and 85, 22,416. Styrenes and styrene derivatives are also suitable for the preparation of homopolymers or copolymers.

In the examples which follow, unless otherwise specified, the reactions were carried out under normal pressure (approx. 1 bar).

EXAMPLE 1

5.76 ml (50 mmols) of benzoyl chloride, 7.53 ml (50 mmols) of N-benzyldimethylamine and 0.1122 g (0.5 mmols) of palladium acetate are added to 100 ml of toluene. Ethylene is passed through the reaction mixture. The mixture is then stirred for 8 hours at 100° C. According to analysis by gas chromatography, the reaction mixture contains 37% of trans-stilbene and 18% of styrene.

EXAMPLES 2–4

Example 1 is repeated using different solvents:

| Example | Solvent | % of trans-stilbene | % of styrene |
| --- | --- | --- | --- |
| 2 | 1,4-Dioxane | 15 | 4 |
| 3 | Cyclohexanone | 13 | 0 |
| 4 | Chlorobenzene | 24 | not determined |

EXAMPLES 5-13

Example 1 is repeated, modifying various parameters of the process, as indicated below:

| Example | | % of trans-stilbene | % of styrene |
| --- | --- | --- | --- |
| 5 | stirred at 80° C. | 14 | 24 |
| 6 | 100 ml of p-xylene, stirred at 120° C. | 60 | 30 |
| 7 | as in Example 6, and 5.75 g (50 mmols) of N—ethylmorpholine added | 54 | 32 |
| 8 | as in Example 6, and 9.27 g (50 mmols) of tri-n-butylamine added | 35 | 28 |
| 9 | as in Example 6, 0.190 g (0.5 mmol) of diacetato-bipyridyl-palladium (II) added | 51 | 24 |
| 10 | as in Example 6, but under a pressure of 0.15 bar, reaction time 2 hours | 55 | 34 |
| 11 | as in Example 6, but under a pressure of 1.28 bar, reaction time 2 hours | 42 | 38 |
| 12 | as in Example 6, 0.0112 g (0.05 mmols) of palladium acetate added | 26 | not determined |
| 13 | as in Example 6, stirred at 130° C. | 60 | not determined |

EXAMPLE 14

34.1 g (0.2 mol) of 4-chlorobenzoyl chloride, 27.04 g (0.2 mol) of N-benzyldimethylamine and 0.448 g (2 mmols) of palladium acetate are added to 400 ml of p-xylene. Ethylene is passed through the reaction mixture, which is stirred for 6 hours at 120° C. The mixture is then filtered and the filtrate is evaporated. The residue is washed on the filter with 200 ml of methanol, in order to remove the amine salt which has been formed. The residue is then recrystallised from 400 ml of cyclohexane. This gives 13.7 g (56% of theory) of trans-4,4′-dichlorostilbene in the form of white crystals; melting point 176.2° C.

EXAMPLE 15

Example 14 is repeated using 30.92 g (0.2 mol) of p-toluyl chloride. The mixture is stirred for 8 hours at 120° C. After working up as described in Example 14 and recrystallisation, 9.3 g (45% of theory) of trans-4,4′-dimethylstilbene are obtained in the form of white, glittering crystals; melting point 184.5° C.

EXAMPLE 16

Example 14 is repeated using 46.13 g (0.2 mol) of 3,4,5-trimethoxybenzoyl chloride. The mixture is stirred for 4.5 hours at 120° C. After working up as described in Example 14 and recrystallising twice (once from 200 ml of cyclohexane and 500 ml of toluene and once from 900 ml of acetone), 10.7 g (30% of theory) of trans-3,3′,4,4′,5,5′-hexamethoxystilbene are obtained in the form of yellow crystals; melting point 220.4° C.

EXAMPLE 17

Example 14 is repeated using 33.7 g (0.2 mol) of 3,4-dimethylbenzoyl chloride. The mixture is stirred for 6.5 hours at 120° C. After working up as described in Example 14 and recrystallising from 250 ml of n-hexane, 10.2 g (43% of theory) of trans-3,3′,4,4′-tetramethylstilbene are obtained in the form of pale yellow crystals; melting point 137.6° C.

EXAMPLE 18

Example 14 is repeated using 34.1 g (0.2 mol) of 3-methoxybenzoyl chloride. The mixture is stirred for 7 hours at 120° C. After working up as described in Example 14 and recrystallising from 200 ml of n-hexane, 10.0 g (42% of theory) of trans-3,3′-dimethoxystilbene are obtained in the form of pale yellow crystals; melting point 98.4° C.

EXAMPLE 19

Example 14 is repeated using 41.89 g (0.2 mol) of 3,4-dichlorobenzoyl chloride. The mixture is stirred for 6¼ hours at 120° C. After working up as described in Example 14 and recrystallising from a mixture of 300 ml of cyclohexane and 250 ml of carbon tetrachloride, 10.1 g (32% of theory) of trans-3,3′,4,4′-tetrachlorostilbene are obtained in the form of pale brown crystals; melting point 187.7° C.

EXAMPLE 20

Example 14 is repeated using 37.11 g (0.2 mol) of 4-nitrobenzoyl chloride and 23.04 g (0.2 mol) of N-ethylmorpholine. The mixture is stirred for 6 hours at 120° C. After working up in accordance with Example 14 and recrystallising from twice 50 ml of N,N-dimethylformamide, 8.65 g (32% of theory) of trans-4,4′-dinitrostilbene are obtained in the form of yellow needles; melting point >300° C.

EXAMPLE 21

Example 20 is repeated using 39.9 g (0.2 mol) of 2-methyl-3-nitrobenzoyl chloride instead of 4-chlorobenzoyl chloride. The mixture is cooled to 5° C. and the crude product is filtered off and washed with 200 ml of 2N HCl. It is then recrystallised first from 200 ml of N,N-dimethylformamide and then from 100 ml of N,N-dimethylformamide. This gives 13.1 g (44% of theory) of trans-2,2′-dimethyl-3,3′-dinitrostilbene in the form of pale yellow crystals; melting point 246.0° C.

EXAMPLE 22

8.43 g (50 mmols) of 4-formylbenzoyl chloride, 11.91 ml (50 mmols) of tri-n-butylamine and 0.1122 g (0.5 mmol) of palladium acetate are added to 100 ml of p-xylene. Ethylene is passed through the mixture, which is stirred for 3 hours at 120° C. The mixture is then extracted by shaking with 100 ml of 2N HCl and is dried with 5 g of magnesium sulfate. After evaporation, the brown residue is chromatographed over silica gel (migrating agent: methylene dichloride). Two products are obtained. The first is distilled in a bulb tube at 55° C./0.002 bar, after evaporating off the methylene dichloride. This gives 0.32 g (5% of theory) of 4-formylstyrene. The second reaction product is recrystallised from benzene/chlorohexane, after removing the methylene dichloride. This gives 0.57 g (10% of theory) of 4,4′-diformylstilbene in the form of yellow leaflets; melting point 168.9° C.

In the procedure according to Examples 14–21, minor amounts of the corresponding styrenes were always formed, but were not isolated.

EXAMPLE 23

1.44 ml (12.5 mmols) of benzoyl chloride, 1.88 ml (12.5 mmols) of N-benzyldimethylamine and 0.0281 g (0.125 mmol) of palladium acetate are added to 25 ml of toluene in a pressure apparatus constructed of glass. The apparatus is flushed with ethylene in order to remove the air. Ethylene is then injected at 10 bar and the mixture is stirred for 4 hours at 120° C. 55% of styrene and 9% of trans-stilbene are formed.

EXAMPLES 24–38

The following proportions of styrene and trans-stilbene are obtained using a procedure analogous to that described in Example 23, but modifying certain process parameters as indicated below:

| Example | | % of styrene | % of trans-stilbene |
|---|---|---|---|
| 24 | stirred at 100° C. | 58 | 7 |
| 25 | stirred at 140° C. | 65 | 8 |
| 26 | stirred at 80° C. | 27 | 2 |
| 27 | 1.44 g (12.5 mmols) of N—ethylmorpholine instead of N—benzyldimethylamine | 2 | 0 |
| 28 | 2.32 g (12.5 mmols) of tri-n-butylamine instead of N—benzyldimethylamine | 27 | 2 |
| 29 | Ethylene pressure 15 bar | 37 | 0 |
| 30 | Ethylene pressure 5 bar | 35 | 4 |
| 31 | 25 ml of dioxane instead of toluene | 41 | 2 |
| 32 | 25 ml of propionitrile instead of toluene | 32 | 2 |
| 33 | 25 ml of ethyl acetate instead of toluene | 42 | 2 |
| 34 | 0.0028 g (0.0125 mmol) of palladium acetate | 8 | 0 |
| 35 | stirred for 2 hours | 40 | not determined |
| 36 | stirred for 6 hours | 57 | 2 |
| 37 | 0.0380 g (0.125 mmol) of bis-(acetylacetonato)-palladium (0) | 48 | 2 |
| 38 | 0.0480 g (0.125 mmol) of dichloro-bis-(benzonitrile)-palladium (II) | 48 | not determined |

EXAMPLE 39

7.73 g (50 mmols) of p-toluyl chloride, 6.76 g (50 mmols) of N-benzyldimethylamine and 0.112 g (0.5 mmol) of palladium acetate are added to 100 ml of toluene. The mixture is stirred for 4 hours at 140° C., under an ethylene pressure of 10 bar. The reaction mixture is filtered and the filtrate is extracted by shaking with 100 ml of 2N HCl and 100 ml of 2N NaOH and then with 30 ml of concentrated aqueous ammonia and 50 ml of water. After drying with magnesium sulfate, the mixture is evaporated and chromatographed over silica gel. After evaporation, 2.1 g (36% of theory) of 4-methylstyrene are obtained in the form of a colourless liquid. This is identified by adding bromine onto the double bond:

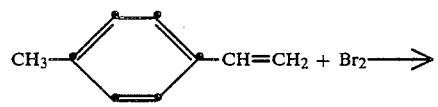

-continued

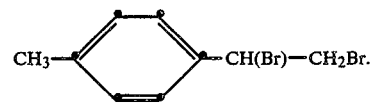

The bromine derivative is obtained in the form of white crystals; melting point 44.7° C.

EXAMPLE 40

Example 39 is repeated using 8.75 g (50 mmols) of 4-chlorobenzoyl chloride instead of p-toluyl chloride. After working up as described in Example 39, 3.8 g (55% of theory) of 4-chlorostyrene are obtained in the form of a colourless liquid, the corresponding bromine derivative of which is precipitated in the form of white crystals, melting point 46.0° C.

EXAMPLE 41

Example 39 is repeated using 8.53 g (50 mmols) of 3-methoxybenzoyl chloride. After working up in accordance with Example 39, 3.2 g (48% of theory) of 3-methoxystyrene are obtained in the form of a colourless liquid, the corresponding bromine derivative of which is precipitated in the form of white crystals, melting point 63.3° C.

EXAMPLE 42

Example 39 is repeated using 11.53 g (50 mmols) of 3,4,5-trimethoxybenzoyl chloride. After working up in accordance with Example 39, 4.1 g (36% of theory) of 3,4,5-trimethoxystyrene are obtained in the form of a yellow liquid. The 3,4,5-trimethoxystyrene is converted into the corresponding bromine derivative (pale yellow needles, melting point 104.1° C.).

EXAMPLE 43

Example 39 is repeated using 10.47 g (50 mmols) of 3,4-dichlorobenzoyl chloride. After working up in accordance with Example 39, 1.6 g (18% of theory) of 3,4-dichlorostyrene are obtained in the form of a yellow liquid. Conversion into the corresponding bromine derivative gives white crystals, melting point 49.3° C.

EXAMPLE 44

Using 8.41 g (50 mmols) of 3,4-dimethylbenzoyl chloride, 3.5 g (53% of theory) of 3,4-dimethylstyrene are obtained in the form of a colourless liquid by a procedure analogous to that described in Example 39. Conversion into the bromine derivative gives pale yellow crystals having a melting point below 40° C.

EXAMPLE 45

Using 9.98 g (50 mmols) of 2-methyl-3-nitrobenzoyl chloride and 5.76 g (50 mmols) of N-ethylmorpholine, 4.15 g (51% of theory) of 2-methyl-3-nitrostyrene are obtained in the form of a pale brown liquid by a procedure analogous to that described in Example 39. Conversion into the bromine derivative gives white crystals, melting point 56.7° C.

EXAMPLE 46

Example 45 is repeated using 9.29 g (50 mmols) of 4-nitrobenzoyl chloride. After working up, 2.2 g (30% of theory) of 4-nitrostyrene are obtained in the form of a yellow liquid. Conversion into the bromine derivative gives white crystals, melting point 74.8° C.

EXAMPLE 47

Example 45 is repeated using 8.44 g (50 mmols) of 4-formylbenzoyl chloride. After working up, 0.7 g (11% of theory) of 4-formylstyrene are obtained in the form of a deep yellow liquid. Conversion into the bromine derivative gives white crystals, melting point 65.9° C.

EXAMPLE 48

2.39 g (12.5 mmols) of 4-chloroformylcinnamonitrile, 1.69 g (12.5 mmols) of N-benzyldimethylamine and 0.0280 g (0.125 mmol) of palladium acetate are added under argon to 25 ml of toluene. The reaction mixture is stirred for 4 hours at 140° C. under an ethylene pressure of 10 bar. The mixture is then extracted by shaking at room temperature with 100 ml of 2N HCl and 100 ml of 2N NaOH and is dried over magnesium sulfate. The solution is then evaporated and the residue is chromatographed over silica gel using methylene dichloride as the migrating agent. The yellow oil thus obtained is dissolved in boiling n-pentane. 0.84 g (44% of theory) of 4-vinylcinnamonitrile are formed at −20° C. in the form of white crystals; melting point 45.8° C.

EXAMPLE 49

1.743 g (6.25 mmols) of biphenyl-4,4'-dicarboxylic acid dichloride, 1.88 ml (12.5 mmols) of N-benzyldimethylamine and 0.0280 g (0.125 mmol) of palladium acetate are added under argon to 25 ml of toluene. The mixture is stirred for 1.5 hours at 115° C. under an ethylene pressure of 10 bar. The mixture is then filtered at room temperature and the filtrate is extracted by shaking with 40 ml of 2N HCl and 40 ml of 2N NaOH. Finally, the mixture is dried with magnesium sulfate and evaporated and the residue is recrystallised once from n-hexane. This gives 0.17 g (12% of theory) of 4,4'-divinylbiphenyl in the form of white crystals; melting point >300° C. (decomposition).

EXAMPLE 50

3.83 g (20 mmols) of 4-chloroformylcinnamonitrile, 2.70 g (20 mmols) of N-benzyldimethylamine and 0.0448 g (0.2 mmol) of palladium acetate are added under argon to 40 ml of p-xylene. Ethylene is passed through the mixture, which is stirred for 23 hours at 130° C. The reaction mixture is then diluted at 130° C. with 40 ml of p-xylene and is filtered. 10 ml of n-hexane are added to the filtrate. Cooling to room temperature gives 0.39 g (15% of theory) of 4,4'-bis-(2-cyanovinyl)-stilbene, melting point 220° C.

APPLICATION EXAMPLES

EXAMPLE I

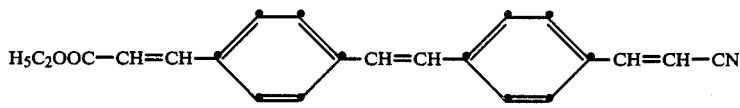

0.68 g (4.44 mmols) of 4-vinylcinnamonitrile, 0.85 g (4.44 mmols) of 4-chloroformylcinnamonitrile and 0.60 g (4.44 mmols) of N-benzyldimethylamine are added under argon to a solution of 9.85 mg (0.044 mmol) of palladium acetate in 19.7 ml of p-xylene. The mixture is stirred for 4 hours at 130° C., cooled to room temperature and filtered. The precipitate is washed with methanol. It is then dissolved in 20 ml of hot N,N-dimethylformamide, 10 ml of water are added and the mixture is cooled to 0° C. This gives 0.62 g (50% of theory) of the above fluorescent brightener; melting point 220° C.

EXAMPLE II

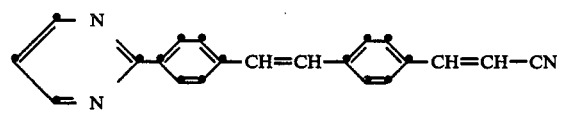

0.84 g (5.49 mmols) of 4-vinylcinnamonitrile, 1.309 g (5.49 mmols) of ethyl 4-chloroformylcinnamate and 0.742 g (5.49 mmols) of N-benzyldimethylamine are added under argon to 12.25 mg (0.0549 mmol) of palladium acetate in 24.5 ml of p-xylene. The mixture is stirred for 5.5 hours at 130° C. The mixture is then diluted with 100 ml of toluene and extracted by shaking with 100 ml of 2N HCl and 100 ml of 2N NaOH. After drying with magnesium sulfate, the solution is evaporated and the crude product is recrystallised first from 100 ml of carbon tetrachloride and then from 50 ml of ethanol. This gives 0.47 g (26% of theory) of the above fluorescent brightener in the form of pale yellow crystals; melting point 155.1° C.

EXAMPLE III

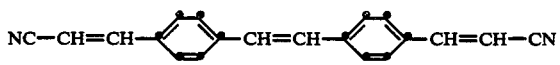

0.0449 g (0.2 mmol) of palladium acetate, 0.1048 g (0.4 mmol) of triphenylphosphine, 4.7 g (20 mmols) of 2-(4-bromophenyl)-pyrimidine [prepared by reacting 4-bromobenzamidine with malondialdehyde in the basic medium], 3.1 g (20 mmols) of 4-vinylcinnamonitrile and 4.47 g (20 mmols) of tri-n-butylamine are added under argon to 20 ml of p-xylene, and the mixture is stirred for 6 hours at 130° C. The crude product obtained is filtered off at room temperature and recrystallised twice from toluene/carbon tetrachloride. This gives 1.9 g (31% of theory) of the above fluorescent brightener in the form of yellow crystals; melting point 290°–291° C.

What is claimed is:

1. A process for the preparation of compounds of the formula Ia or Ib $$Z-CH=CH-Z_1 \quad (Ia)$$

or $$CH_2=CH-Z_2-CH=CH_2, \quad (Ib)$$

in which Z represents unsubstituted or substituted phenyl or naphthyl, $Z_1$ represents hydrogen or has the same meaning as Z and $Z_2$ represents unsubstituted or substituted phenylene, naphthylene or p-biphenylene or an unsubstituted or substituted stilbene radical, which comprises reacting ethylene, under a pressure of 0.1 to 20 bar, in the presence of a base and with the addition of palladium metal or palladium compounds which form phosphorus-free labile palladium(O) compounds under the reaction conditions, as a catalyst, with a compound of the formula II or III Z—COX(II) or XOC—Z₂COX(III)

in which Z and Z₂ have the meanings indicated under formula Ia and Ib, respectively, and X represents chlorine, bromine or iodine.

2. A process according to claim 1, wherein a compound of the formula II or III in which X represents chlorine, is used.

3. A process according to claim 1, wherein the acid halide used is biphenyl-4,4'-dicarboxylic acid dichloride, stilbene-4,4'-dicarboxylic acid dichloride or a compound of the formula IIa

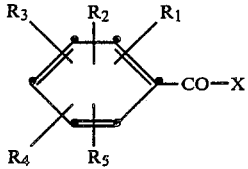

in which X represents chlorine, R₁ represents hydrogen, formyl, methyl, methoxy, Cl, Br or nitro, R₂ represents hydrogen, methyl, methoxy, Cl or Br, R₃ represents hydrogen or methoxy and R₄ and R₅ represent hydrogen, or in which X represents chlorine, R₁ represents —CH=CHCN, —CH=CHCOOCH₃ or —CH=CH-COOC₂H₅ and R₂ to R₅ represent hydrogen.

4. A process according to claim 1, wherein the catalyst used is PdCl₂, PdBr₂, Pd(OOCCH₃)₂,

Pd(OOCCH₃)₂(2,2'-bipyridyl), PdCl₂(NC-phenyl)₂, bis-(dibenzylideneacetone)-palladium(O) or bis-(cyclohexyl isonitrile)-palladium(O).

5. A process according to claim 1, wherein the catalyst used is PdCl₂, palladium acetate or bis-(benzylideneacetone)-palladium(O).

6. A process according to claim 1, wherein the reaction with the acid halides of the formula II is carried out under a pressure between 0.1 and 1 bar.

7. A process according to claim 6 for the preparation of compounds of the formula Ia in which Z₁ represents unsubstituted phenyl or naphthyl, wherein the reaction is carried out under a pressure of 1 bar.

8. A process according to claim 1 for the preparation of the compound of the formula

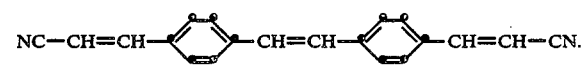

9. A process according to claim 1 for the preparation of the compound of the formula

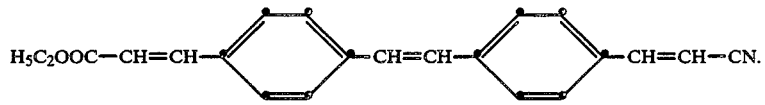

10. A process according to claim 1, wherein the reaction with the acid halides of the formula II or III is carried out under a pressure between 5 and 15 bar.

11. A process according to claim 10 for the preparation of compounds of the formula Ia in which Z₁ represents hydrogen, or of the formula Ib in which Z₂ represents unsubstituted or substituted phenylene, naphthylene or p-biphenylene, wherein the reaction is carried out under a pressure of 10 bar.

12. A process according to claim 1, wherein the catalyst is used in an amount of 0.001 to 3 mol %, based on the compound of the formula II or III.

13. A process according to claim 1, wherein the reaction is carried out at a temperature between 0° and 200° C. and in the presence of an organic solvent which is inert towards the reactants.

14. A process according to claim 13, wherein the solvent used is anisole, xylenes or toluene.

15. A process according to claim 1, wherein the base used is a compound of the formula VI

in which Q₅ represents 4-chlorobenzyl, 4-methylbenzyl, 4-methoxybenzyl or benzyl and Q₆ and Q₇ each represent alkyl having 1-4 C atoms, or in which Q₅, Q₆ and Q₇ each represent alkyl having 3-12 C atoms.

16. A process according to claim 1, wherein the base used is N-benzyldimethylamine, N-ethylmorpholine or tri-n-butylamine.

* * * * *